(12) United States Patent　　(10) Patent No.: US 12,636,192 B2

Goldshleger et al.　　(45) Date of Patent: May 26, 2026

---

(54) BI-RADIAL PATIENT INTERFACE

(71) Applicant: ALCON INC., Fribourg (CH)

(72) Inventors: Ilya Goldshleger, Ladera Ranch, CA (US); Jeremy Dong, Aliso Viejo, CA (US); Tibor Juhasz, Corona Del Mar, CA (US); Wesley William Lummis, Rancho Santa Margarita, CA (US); Ferenc Raksi, Mission Viejo, CA (US)

(73) Assignee: ALCON INC., Fribourg (CH)

( * ) Notice: Subject to any disclaimer, the term of this patent is extended or adjusted under 35 U.S.C. 154(b) by 163 days.

(21) Appl. No.: 18/756,268

(22) Filed: Jun. 27, 2024

(65) Prior Publication Data

US 2024/0350317 A1　　Oct. 24, 2024

Related U.S. Application Data

(60) Continuation of application No. 18/068,323, filed on Dec. 19, 2022, now Pat. No. 12,048,651, which is a continuation of application No. 17/064,141, filed on Oct. 6, 2020, now Pat. No. 11,559,436, which is a division of application No. 16/419,936, filed on May 22, 2019, now Pat. No. 11,395,765, which is a (Continued)

(51) Int. Cl.

| | |
|---|---|
| *A61F 9/009* | (2006.01) |
| *A61B 3/103* | (2006.01) |
| *A61B 3/107* | (2006.01) |
| *A61B 3/117* | (2006.01) |
| *A61B 3/14* | (2006.01) |
| *A61F 9/00* | (2006.01) |
| *A61F 9/008* | (2006.01) |

(52) U.S. Cl.
CPC .............. *A61F 9/009* (2013.01); *A61B 3/103* (2013.01); *A61B 3/107* (2013.01); *A61B 3/117* (2013.01); *A61B 3/1173* (2013.01); *A61B 3/14* (2013.01); *A61F 2009/0052* (2013.01); *A61F 2009/00851* (2013.01)

(58) Field of Classification Search
CPC ........... A61B 3/12; A61B 3/125; A61B 3/107; A61B 3/117; A61F 9/009; A61F 2009/00872
See application file for complete search history.

(56) References Cited

U.S. PATENT DOCUMENTS

| | | | |
|---|---|---|---|
| 4,966,452 A | 10/1990 | Shields | |
| 6,019,472 A * | 2/2000 | Koester | .................. A61F 9/009 |
| | | | 351/219 |

(Continued)

FOREIGN PATENT DOCUMENTS

| | | |
|---|---|---|
| JP | H02299653 A | 12/1990 |
| JP | H08117266 A | 5/1996 |

*Primary Examiner* — Camtu T Nguyen

(57) ABSTRACT

To improve the precision of ophthalmic surgical procedures by reducing corneal wrinkling, a patient interface for an ophthalmic system can include an attachment portion, configured to attach the patient interface to a distal end of the ophthalmic system; a contact portion, configured to dock the patient interface to an eye; and a contact element, coupled to the contact portion, configured to contact a surface of a cornea of the eye as part of the docking of the patient interface to the eye, and having a central portion with a central radius of curvature Rc and a peripheral portion with a peripheral radius of curvature Rp, wherein Rc is smaller than Rp.

15 Claims, 6 Drawing Sheets

Related U.S. Application Data continuation of application No. 15/892,145, filed on Feb. 8, 2018, now abandoned, which is a division of application No. 13/757,236, filed on Feb. 1, 2013, now Pat. No. 10,335,315.

(56) References Cited

U.S. PATENT DOCUMENTS

| | | | |
|---|---|---|---|
| 8,500,723 B2 * | 8/2013 | Frey | A61F 9/009 |
| | | | 606/4 |
| 2011/0304819 A1 * | 12/2011 | Juhasz | A61B 3/13 |
| | | | 351/205 |
| 2012/0016349 A1 * | 1/2012 | Brownell | A61F 9/009 |
| | | | 606/4 |
| 2013/0165911 A1 * | 6/2013 | Raksi | A61F 9/009 |
| | | | 606/4 |
| 2018/0303664 A1 * | 10/2018 | Accurso | A61F 9/009 |

* cited by examiner

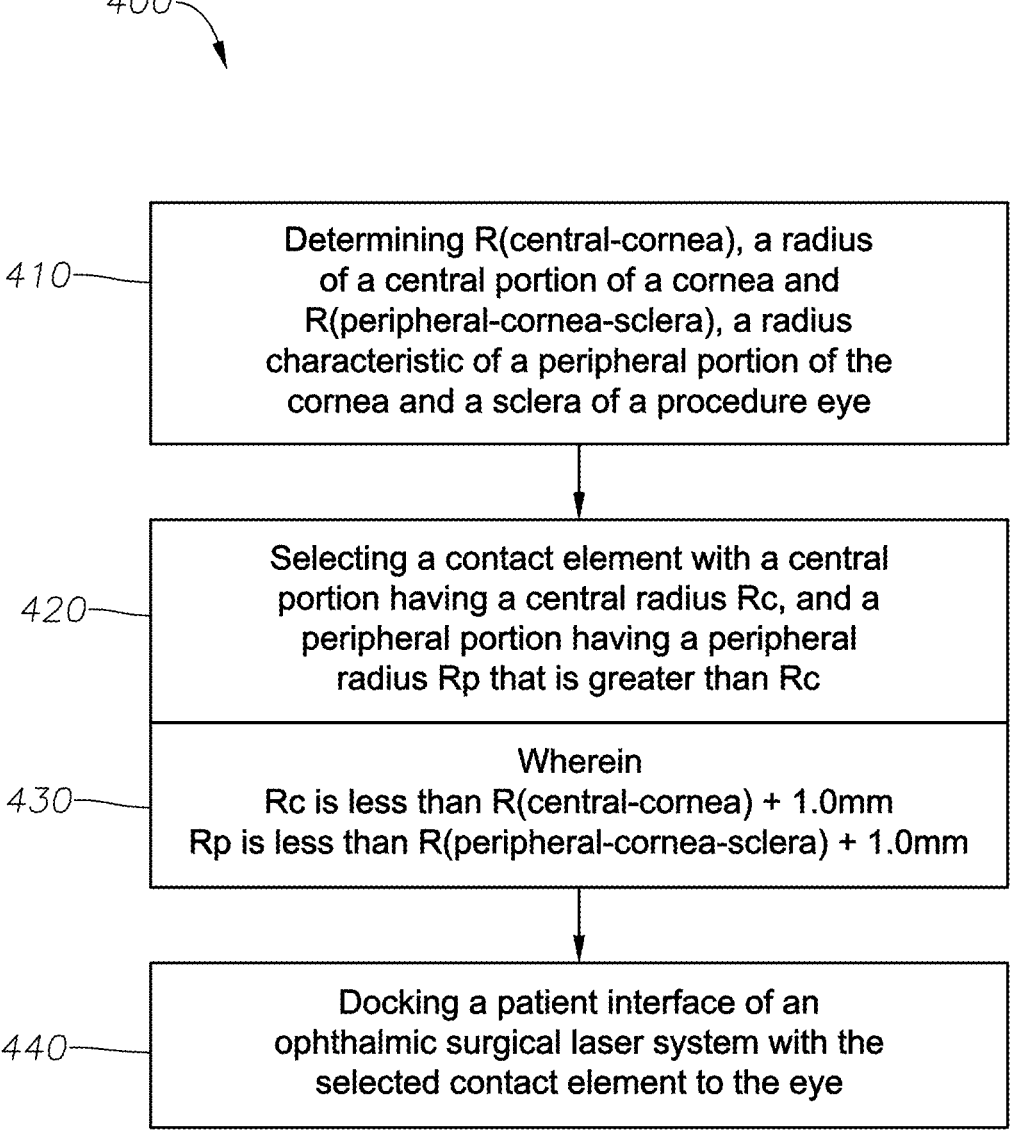

400

410 — Determining R(central-cornea), a radius of a central portion of a cornea and R(peripheral-cornea-sclera), a radius characteristic of a peripheral portion of the cornea and a sclera of a procedure eye 420 — Selecting a contact element with a central portion having a central radius Rc, and a peripheral portion having a peripheral radius Rp that is greater than Rc 430 — Wherein
Rc is less than R(central-cornea) + 1.0mm
Rp is less than R(peripheral-cornea-sclera) + 1.0mm 440 — Docking a patient interface of an ophthalmic surgical laser system with the selected contact element to the eye

FIG. 5

BI-RADIAL PATIENT INTERFACE

RELATED APPLICATIONS

This application is a continuation application claiming benefit to U.S. patent application Ser. No. 18/068,323, filed Dec. 19, 2022, which is a continuation of U.S. patent application Ser. No. 17/064,141, filed Oct. 6, 2020 (now U.S. Pat. No. 11,559,436), which is a divisional of U.S. patent application Ser. No. 16/419,936, filed May 22, 2019 (now U.S. Pat. No. 11,395,765), which is a continuation of U.S. patent application Ser. No. 15/892,145, filed Feb. 8, 2018, which is a divisional of U.S. patent application Ser. No. 13/757,236, filed Feb. 1, 2013 (now U.S. Pat. No. 10,335,315). All applications are incorporated herein by reference in their entirety.

BACKGROUND

Field of Invention

This patent document relates to patient interfaces that attach an ophthalmic system to an eye for anterior segment eye procedures. More particularly, this patent document relates to bi-radial patient interfaces that reduce a deformation of a cornea of the procedure eye.

Description of Related Art

This patent document describes examples and embodiments of techniques and devices for securing an ophthalmic system to an eye. The ophthalmic system may be an ophthalmic surgical laser system to perform an anterior segment eye procedure, such as a cataract procedure. These devices are often referred to as patient interfaces. A patient interface serves to connect and to couple the ophthalmic system and the eye of the patient, thus their performance is an important controlling factor of the precision and success of the ophthalmic procedures. Therefore, improvements in patient interfaces can lead to improvements in the precision and reliability of ophthalmic procedures.

SUMMARY

Briefly and generally, embodiments of the present invention are capable of reducing corneal wrinkling, one of the factors that hinder the precision of ophthalmic surgical procedures. The causes of corneal wrinkling include a pressure exerted by the weight of the patient interface and an objective of an optical system on the eye; a compressive force, generated by a negative pressure of a suction system to immobilize the patient interface relative to the eye; a mismatch between the radius of curvature of the patient interface and that of the cornea of the eye; the complex shape of the surface of the cornea; and the variation of the corneal radius of curvature from patient to patient.

To improve the precision of ophthalmic surgical procedures by reducing corneal wrinkling, a patient interface for an ophthalmic system according to embodiments of the present invention can include an attachment portion, configured to attach the patient interface to a distal end of the ophthalmic system; a contact portion, configured to dock the patient interface to an eye; and a contact element, coupled to the contact portion, configured to contact a surface of a cornea of the eye as part of the docking of the patient interface to the eye, and having a central portion with a central radius of curvature Rc and a peripheral portion with a peripheral radius of curvature Rp, wherein Rc is smaller than Rp.

Embodiments of a method of docking a patient interface of an ophthalmic surgical laser system to an eye can include: determining R(central-cornea), a radius of curvature of a central portion of a cornea of the eye, and R(peripheral-cornea-sclera), a radius of curvature characteristic of a peripheral portion of the cornea and a sclera of the eye; selecting a contact element with a central portion having a central radius of curvature Rc and a peripheral portion having a peripheral radius of curvature Rp that is greater than Rc, wherein Rc is less than R(central-cornea)+1 mm, and Rp is less than R(peripheral-cornea-sclera)+1 mm; and docking the patient interface of the ophthalmic surgical laser system with the selected contact element to the eye.

BRIEF DESCRIPTION OF THE DRAWINGS

FIG. 5 illustrates a method of using a patient interface with a bi-radial contact element.

DETAILED DESCRIPTION

Figure 1:
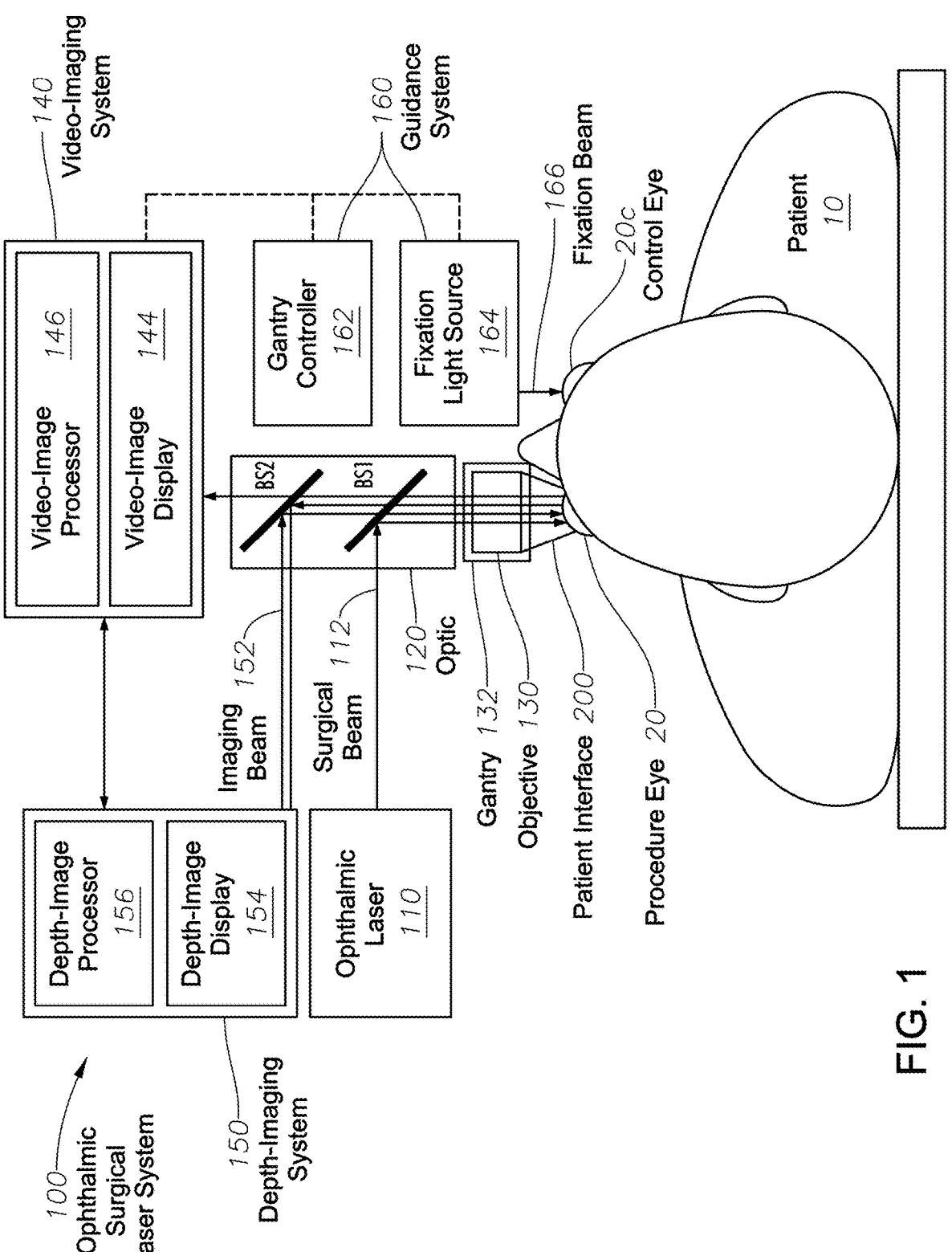
FIG. 1 illustrates an ophthalmic surgical laser system.

Some laser eye surgical procedures, such as corneal refractive corrections, and laser-assisted lens photodisruptions and capsulotomies, may benefit from immobilizing the procedure eye relative to the ophthalmic surgical laser system during the procedure. Some ophthalmic surgical laser systems make use of a so-called patient interface to carry out this task. A proximal portion of the patient interface can be attached to a distal end of the surgical laser system, such as to its objective. A distal portion of the patient interface can include a contact lens. The patient interface can be docked to the eye by pressing it to the eye and then applying suction to a space between the patient interface and the eye. When the patient interface is docked to the eye, the contact lens is pressed against the cornea of the eye. The pressure and suction of the patient interface holds the eye steady relative to the surgical laser system, and the contact lens provides a well-controlled optical coupling to the eye. Both these attributes enable a high precision directing and focusing of the laser beam to predetermined target locations within the eye.

Some patient interfaces use flat contact lenses, also called applanation plates. Others include single-radius of curvature curved contact lenses. To prevent the slipping and rolling of the eye, caused by the slipperiness of the tear film covering the eye, these contact lenses are pressed against the cornea of the eye by mechanical forces and by applying suction by a vacuum system to a surrounding suction ring.

While using single-radius of curvature contact lenses has the benefit of providing a well-defined and simple optical element for optimizing the beam properties of the laser beam of the ophthalmic system, and possibly a reference plane to direct the surgical laser with precision, their use can also lead to problems that include the following.

(1) Bubbles are often trapped under the contact lens during docking. To avoid this bubble formation, the radius of curvature of the single-radius-of-curvature contact lenses is typically chosen to be larger than that of the cornea. A typical corneal radius of curvature in the central portion (in the central-cornea) is in the range of 7.2-8.0 mm, quite often close to 7.6 mm. Accordingly, the radius of curvature of single-radius-of-curvature contact lenses is often chosen to be distinctly larger than these values, often in the 10-15 mm range. The 10-15 mm range for the radius of curvature can be useful to optimize the wavefront of the laser beam 112 and to minimize its aberrations.

However, such a large mismatch of the radius of curvature of the contact lens and that of the cornea can lead to the problem that upon docking to the eye the contact lens flattens and thus wrinkles the surface of the cornea. These wrinkles can distort the laser beam, leading to increased scattering of the beam, and reducing its power below a photodisruption threshold, possibly making the important capsulotomy cuts of the cataract surgery incomplete. If, in response, the power of the laser beam is increased to overcome the increased scattering by the wrinkles, then the higher power can damage the photosensitive tissues of the eye, such as the retina, especially when scanning the beam through regions where the cornea is not wrinkled. Wrinkling can also reduce the precision of the targeting of the laser beam.

(2) Using single-radius-of-curvature contact lenses can wrinkle the cornea for the additional reason that the frontal surface of the eye is more complex than that of the single radius contact lens. It includes a central-cornea with a radius of curvature R(central-cornea) in the 7-8 mm range, with a typical radius of curvature of about 7.6 mm. Surrounding the central-cornea is a peripheral-cornea, whose radius of curvature R(peripheral-cornea) can gradually increase from 8 mm up to 11 mm. Surrounding the peripheral-cornea is the sclera, whose radius of curvature R(sclera) is markedly different from the central-cornea: it is in the 9-14 mm range, often in the 9.5-12 mm range. A single-radius-of-curvature contact lens and a frontal eye surface that has two or even three distinct radii are mismatched to a degree that upon docking the patient interface on the eye, the mismatch can cause a substantial wrinkling of the cornea.

(3) The mismatched radius of curvature of the contact lens and its single-radius-of-curvature structure can not only wrinkle the cornea but can also cause internal deformations since the support system of the internal lens of the eye is very soft. Therefore, the docking of a single-radius of curvature, mismatched contact lens typically shifts and tilts the lens of the eye relative to the optical axis of the eye. This displacement and tilt may make the cuts of a typical cataract surgery, including the critical capsulotomy cut on the capsular bag and the cataract surgical cut-pattern inside the lens, off-center and distorted, leading to a deterioration of the optical outcome of the cataract procedure.

For all these reasons, developing new types of contact lenses that do not have a single-radius-of-curvature structure and a mismatched radius of curvature can improve the performance of ophthalmic surgical laser systems. Embodiments of the present invention offer solutions for the here-outlined problems and challenges.

FIG. 1 illustrates an imaging-guided ophthalmic surgical laser system 100. The surgical laser system 100 can include an ophthalmic laser 110 that can generate a surgical laser beam 112. The surgical laser beam 112 can be a pulsed beam with pulse length in the 1-1,000 femtosecond range. The laser beam 112 can have a power sufficient to cause photo-disruption in an ophthalmic target tissue. The laser beam 112 can be coupled into an optic 120 via a beam splitter BS1. Optic 120 can focus and direct the laser beam 112 to a target point in a target region of a procedure eye 20 of a patient 10 through an objective 130. With the help of scanning mirrors and actuators, optic 120 can also scan the laser beam 112 through a sequence of target points to cut the eye tissue along a surgical cut pattern.

The procedure eye 20 can be immobilized relative to the surgical laser system 100 with a patient interface 200 to prevent involuntary movements of the eye 20 and thus to enhance the precision and reliability of the surgical procedure. Patient interface (PI) 200, attached to the objective 130 at a proximal end, can be docked to the eye 20 with a vacuum suction system. To dock the PI 200 to the eye 20, the objective 130 can be aligned with the eye 20 by a gantry 132.

Surgical procedures can be aided by including various imaging systems into the surgical laser system 100. A video imaging system 140, such as a video-microscope, can be included in the surgical laser system 100 that images the eye 20 and displays it on a video-image display 144. In some embodiments, the video-imaging system 140 can also include a video-image processor 146 to process the video image. Such video-imaging systems 140 can provide a frontal view of the eye 20, but typically provide limited information of the depth, or z-directional structure of the eye 20.

In order to provide depth, or z-directional, imaging, the surgical laser system 100 can include a depth-imaging system 150. The depth-imaging system 150 can include an optical coherence tomography (OCT) imaging system, a Scheimpflug imaging system, a slit-lamp system, or equivalents. The depth-imaging system 150 can emit an imaging beam 152 that is coupled into the optic 120 by a beam splitter BS2 and directed to the target by the optic 120. The imaging beam 152 can be reflected from the eye 20 and returned to the depth-imaging system 150 where it gets analyzed and displayed on a depth-image display 154. In some embodiments, a depth-image processor 156 can be included to process the depth-image, such as to recognize edges and to reduce noise. In some surgical laser systems 100 the video-imaging system 140 and the depth-imaging system 150 can be coupled.

Finally, the surgical laser system 100 can also include a docking guidance system 160 to guide the docking of the patient interface 200. The docking guidance system 160 can include a gantry controller 162 that can move the gantry 132 to align the objective 130 with the eye 20. In some embodiments, a fixation light source 164 can be also included to project a fixation light beam 166 into a control eye 20c or into the eye 20 through the objective 130. The fixation light beam 166 can be adjusted to direct the patient to rotate his/her eyes to further improve the alignment with the objective 130. Some of the operations of the guidance system 160 can be computer-controlled and can be based on the output of the video-image processor 146 and the depth-image processor 156.

Figure 2A:
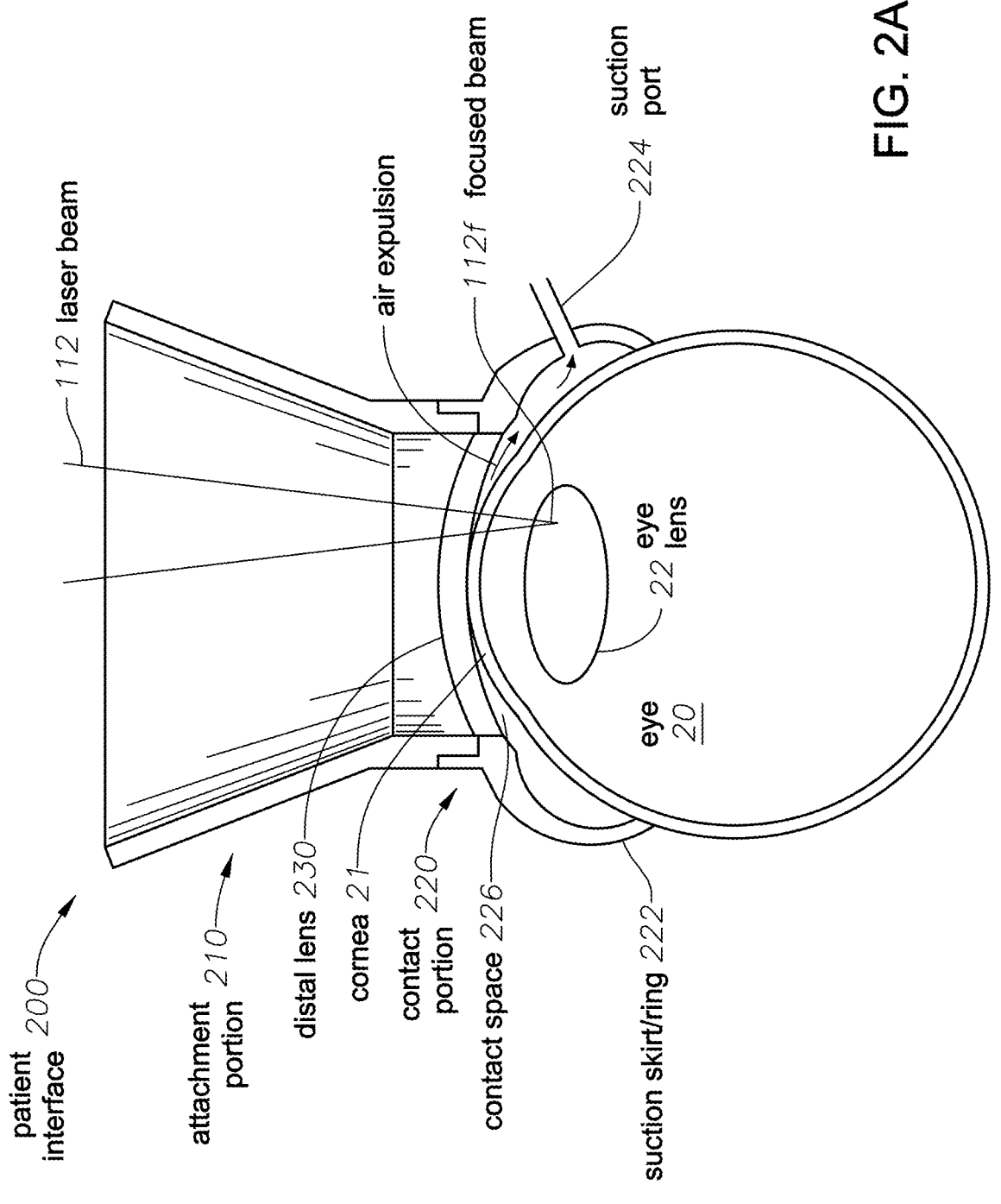
FIGS. 2A-B illustrate the wrinkling of the cornea during docking with some patient interfaces.
Figure 2B:
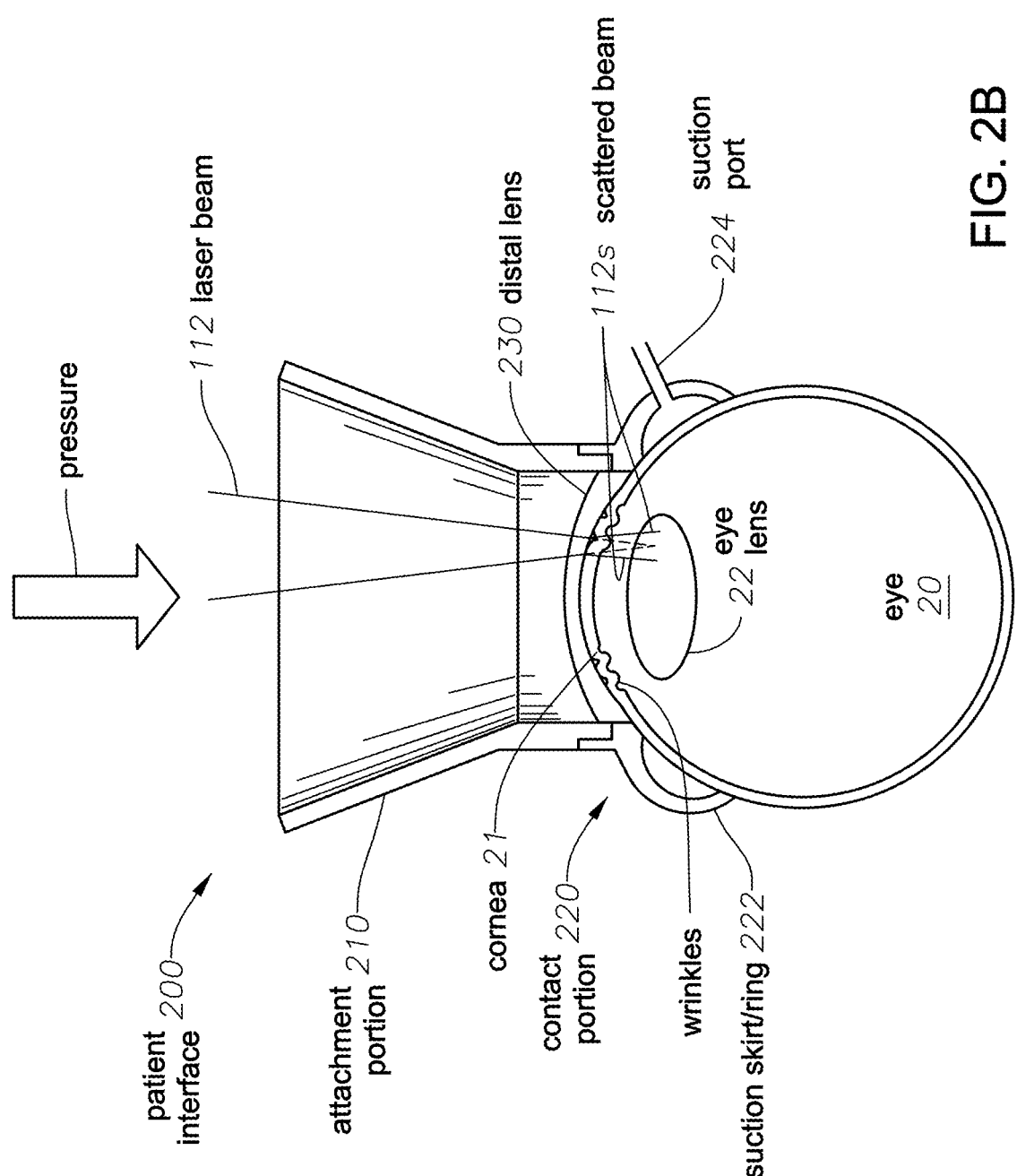

FIGS. 2A-B illustrate the docking of the patient interface 200 on the eye 20 in more detail. The patient interface (PI) 200 can include an attachment portion 210 to attach the PI 200 to the objective 130, a contact portion 220 that is docked to the eye 20, and a distal lens 230 that optically couples the surgical laser beam 112 and the imaging beams into a cornea 21 of the eye 20. The contact portion 220 can include a suction skirt or suction ring 222 that has a suction port 224. This suction port 224 can be coupled to a vacuum or suction system to apply vacuum or negative pressure that expels air from a contact space 226, thus pressing the distal lens 230 onto the cornea 21.

In an ideal operation, the laser beam 112 propagates through the optic 120, objective 130 and distal lens 230 to arrive to the target of the ophthalmic surgical procedure, such as a lens 22 of the eye as a focused beam 112*f,* and to form precise surgical cuts. However, FIG. 2B illustrates that under some circumstances the pressure of docking can wrinkle the cornea 21. These wrinkles can scatter the laser beam 112 into a scattered beam 112*s* that has lower power at the target and thus may be unable to perform the surgical cuts. Also, the scatter laser beam 112*s* may be deflected or misdirected by the wrinkles. The lowered beam power and misdirection can have various negative consequences, as discussed earlier.

Figure 3:
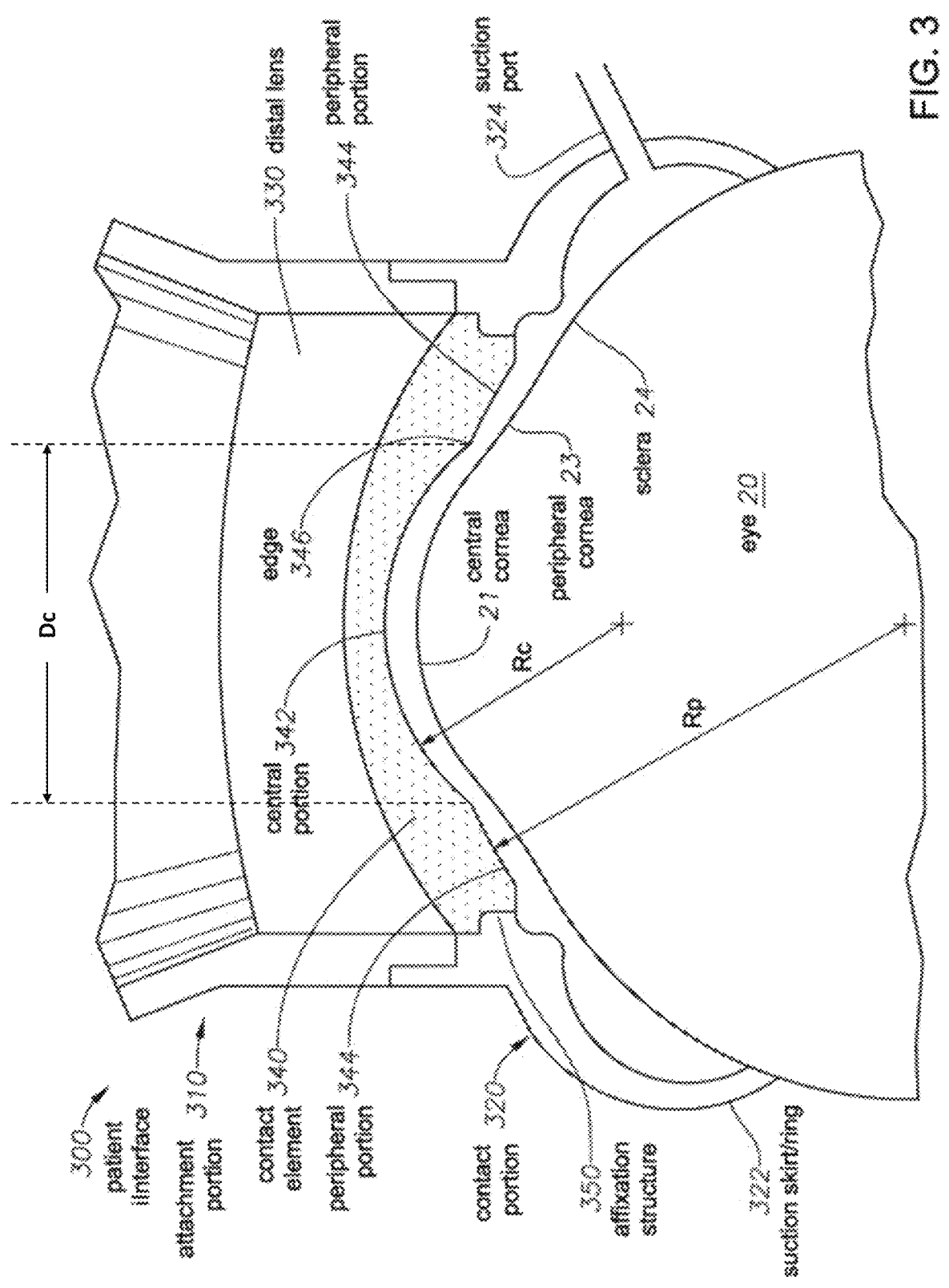
FIG. 3 illustrates a one-piece patient interface with a bi-radial contact element.

FIG. 3 illustrates a patient interface (PI) 300 according to embodiments of the invention that is configured to reduce the corneal wrinkling related to docking. The patient interface 300 can include an attachment portion 310, configured to attach the patient interface 300 to a distal end of the ophthalmic surgical laser system 100, in particular to its objective 130. The attachment portion 310 can include a bayonet lock, a snap-on lock, or locking flanges, for example. It can be made of plastic or another flexible material.

The PI 300 can also include a contact portion 320, configured to dock the patient interface 300 to the eye 20. The contact portion 320 can include a suction skirt or suction ring 322 that has a suction port 324. The suction port can be attachable to a vacuum or suction system that can apply negative pressure or suction to a contact space between the PI 300 and the cornea of the eye. With this design, the contact portion 320 can attach the PI 300 to the eye and thus immobilize the eye 20 relative to the surgical laser system 100. The PI 300 can also include a distal lens 330 that can optically couple the laser beam 112 into the cornea in a controlled manner. The distal lens 330 can be a rigid or hard lens with well-defined optical characteristics.

In addition to these elements, the patient interface 300 can also include a contact element 340 that is coupled to the contact portion 320. The contact element 340 can be configured to contact a surface of the cornea as part of the docking of the patient interface 300 to the eye. Embodiments of the contact element 340 can reduce the corneal wrinkling by having a structure different from existing contact lenses in that they can have two portions with different radii of curvatures: a central portion 342 with a central radius of curvature Rc and a peripheral portion 344 with a peripheral radius of curvature Rp, wherein Rc is smaller than Rp. Such designs can have various advantages.

(1) Structure matching: Because of the added design degree of freedom of having two radii instead of one, in general the bi-radial structure of the contact element 340 can mirror and accommodate the complex frontal surface of the eye better than single-radius-of-curvature contact elements, thus reducing wrinkling compared to a single-radius-of-curvature contact element.

(2) Radius matching: In addition to the advantage of having a bi-radial structure in general, in some embodiments in particular the radii Rc and Rp can be chosen to be close to the central-corneal radius of curvature R(central-cornea) and the scleral radius of curvature R(sclera), thus further reducing the previously discussed radial mismatch, flattening and wrinkling. In some embodiments, Rc can be in the range of 6.6 mm-9.1 mm and Rp in the range of 8.8 mm-10.8 mm. In other embodiments, Rc can be in the range of 7.1 mm-8.1 mm and Rp in the range of 9.3 mm-10.3 mm. It is recalled here that the central corneal radius of curvature R(central-cornea) is typically in the range of 7-8 mm, often close to 7.6 mm, and the radius of curvature of the sclera R(sclera) is typically in the range of 9-14 mm, often in the range of 9.5-12 mm. Therefore, the above listed ranges of Rc and Rp can provide a close match between the patient interface 300 and the central-cornea 21 and the sclera 24. Since from now on the corneal structure will be discussed in more detail and resolution, label 21 will refer only to the central-cornea and label 23 to the peripheral-cornea, as shown in FIG. 3.

It is noted here that the radii of the frontal eye surface have a broad distribution in various patient groups. A very small percentage of patients have been identified with radii outside the above ranges: they constitute the tails of the radius distribution. Therefore, statements about ranges of radii here refer to a representative range of the large majority of the patient population, and may not include the farthest outlying few percent tail of the distribution.

Bi-radial patient interfaces whose radii approximately match the radii of the central cornea and that of the sclera offer advantages over existing single-radius-of-curvature, mismatched patient interfaces. Approximately matching the central radius of curvature Rc to that of the central cornea R(central-cornea) can efficiently reduce or even eliminate the wrinkling of the cornea, since docking the contact element 340 does not exert a flattening effect on the central cornea anymore. Also, approximately matching the peripheral radius of curvature Rp to R(sclera) can allow the efficient suction and removal of bubbles, formed during docking, along the contact surface between the peripheral portion 344 and the cornea. The removal of the bubbles can be further eased and assisted by applying lubricants to the contact surface.

Given the complex frontal surface of the eye, in some embodiments, Rp may not be matched to the radius of curvature of the sclera R(sclera) alone, but rather can be chosen to be characteristic of both the peripheral-corneal radius of curvature R(peripheral-cornea) and scleral radius of curvature R(sclera).

In the above discussions, Rc and Rp represent radii of curvatures. The central portion 342 of the contact element 340 also has a lateral central-diameter Dc. This lateral central-diameter Dc is different from the radii of curvature: in a Cartesian coordinate system with its Z axis along the optical axis of the objective 130, the radii of curvature Rc and Rp are defined in an XZ or a YZ plane, whereas the lateral central-diameter Dc is defined in the XY plane. In addition, the peripheral portion 344 of the contact element can have a peripheral-diameter Dp.

To discuss the relation of the diameters Dc and Dp to the corneal diameters, it is recalled here that a diameter of the central-cornea 21 D(central-cornea) can be in the 6-9 mm range and a diameter of the peripheral-cornea D(peripheral-cornea) in the 10-12 mm range, often about 11 mm. D(peripheral-cornea) is where the peripheral-cornea 23 meets the sclera 24 and thus a relatively well-defined quantity. On the other hand, the radius of curvature of the cornea varies from its value R(central-cornea) in the central-cornea 21 somewhat gradually towards its value R(peripheral-cornea) in the peripheral-cornea 23. Therefore, the transition line between these portions may not be sharp and thus the value of D(central-cornea) may depend on the particular definition adopted.

In light of these values, some matching embodiments of the contact element 340 can have a central-diameter Dc in the 6-9 mm range, in some cases in the 8-9 mm range. Embodiments can also have a peripheral-diameter Dp in the 10-14 mm.

For completeness of the discussion, here we reproduce that R(central-cornea) typically falls in the 7-8 mm range, with a average value of about 7.6 mm; R(peripheral-cornea) in the 8-11 mm range; and R(sclera) in the 9-14 mm range, often in the 9.5-12 mm range.

Returning to the discussion of the diameters, FIG. 3 illustrates that in some embodiments, while the central-diameter Dc of the contact element 340 may track the complex frontal eye surface in general, but it may not be precisely aligned or matched with either D(central-cornea) or D(peripheral-cornea). Rather, the central-diameter Dc can fall between these values. Embodiments with this feature may have an additional advantage beyond (1) structure matching, and (2) radius matching, as discussed next.

(3) Lateral stretching: As shown in FIG. 3, in some embodiments an edge 346 can be formed at the central-diameter Dc, where the central portion 342 and the peripheral portion 344 are joined, because the central radius Rc is different from the peripheral radius Rp. In embodiments where D(central-cornea)<Dc<D(peripheral-cornea), upon docking, the edge 346 lands on the peripheral-cornea 23. Since the radius of curvature of the central portion Rc is not equal to the radius of curvature of the peripheral-cornea R(peripheral-cornea), the contact element 340 at the edge 346 may not smoothly match the peripheral-cornea 23, but rather press or wedge into it as the docking starts. As the docking proceeds, this wedged edge 346 can laterally stretch the peripheral-cornea 23 and thus the central-cornea 21, in a sense "ironing out" wrinkles that may have started to form by the docking pressure. This is an additional advantage of the bi-radial design of the contact element 340 that is especially effective when the edge 346 with the central-diameter Dc is larger than the diameter of the central-cornea 21: D(central-cornea)<Dc, and smaller than the diameter of the peripheral-cornea D(peripheral-cornea): Dc<D(peripheral-cornea). As discussed above, for most eyes, D(central-cornea) falls in the 6-9 mm range, and D(peripheral-cornea) in the 10-12 mm range, thus the above inequality broadly translates to Dc falling in the 6-12 mm range. In some embodiments Dc may fall in the 8-10 mm range.

This stretching or ironing functionality can be especially effective if a contact element 340 is chosen for a patient that has a central radius of curvature Rc that is slightly smaller than the radius of curvature of the central-cornea R(central-cornea) of the patient.

To sum up the above considerations: the bi-radial contact elements 340 can provide a performance superior to the existing contact lenses, whose non-matching, single-radius-of-curvature design flattens and wrinkles the cornea, because embodiments of the here-described bi-radial contact elements can offer one or more of (1) structure matching, (2) radius matching, and (3) lateral stretching of the cornea, all of these effects being capable of reducing the wrinkling of the cornea.

Some embodiments of the contact element 340 can go even further and match the three-portion structure of the anterior surface of the eye. In some embodiments, the contact element 340 can have a central portion with a central-radius of curvature Rc in the 7-9 mm range to align with the central-cornea 21, an intermediate portion with an intermediate radius of curvature Ri in the 8-12 mm range to align with the peripheral-cornea 23 and a peripheral portion with a peripheral radius of curvature Rp in the 10-14 mm range to align with the sclera. In some embodiments these three radii are related as: Rc<Ri<Rp. Such a contact element that matches the structure of the frontal eye surface and approximates its three radii may cause an even more limited corneal wrinkling. Such patient interfaces and contact elements can be termed "tri-radial".

In addition, as discussed at (3) above, if one or both of the diameters separating the three regions of such a tri-radial contact element are not aligned with D(central-cornea) and D(peripheral-cornea), that can lead to a beneficially enhanced lateral stretching effect.

In some embodiments, the contact portion 320 can include an escape structure to assist an expulsion of air from the contact space between the contact element 340 and the cornea. This escape structure can take various forms, such as radial channels or a rounding of the edge 346 along short arc segments.

The bi-radial structure of the contact element 340 has a further aspect: during docking the bi-radial structure can assist the centering of the patient interface 300. In a case when the bi-radial contact element 340 makes its initial contact with the cornea in a de-centered position, the edge 346 and the bi-radial contacting surfaces can exert lateral forces that can laterally move the eye until it reaches a more centered position. This self-centering can also be made more effective if a lubricating liquid is applied to the contact surface.

In some embodiments, the distal lens 330 can be rigid or have reduced flexibility. The distal lens 330 can accommodate a proximal surface of the contact element 340, preventing a more than 5% radial deformation of the contact element 340 upon docking to the eye ($\Delta R_c/R_c < 5\%$). In some embodiments, this is achieved by employing a distal lens 330 with a distal surface radius of curvature that is approximately matched to a proximal surface radius of curvature of the contact element 340. As shown in FIG. 3, the proximal surface radius of curvature of the contact element 340 is larger than that of the central radius $R_c$.

In some embodiments, the contact portion 320 may include an affixation structure 350 to affix the contact element 340 to the contact portion 320 along a perimeter. The affixation structure 350 can be configured to prevent a more than 5% lateral deformation of the contact element 340 upon docking to the eye. To achieve this functionality, the affixation structure 350 can include an affixation groove, a support rim, an insertion structure, an interlocking structure, a slide-in structure, a pop-in structure, or a lock-in structure.

In some embodiments where the distal lens 330 can limit the radial deformation of the contact element 340 and the affixation structure 350 can limit its lateral expansion, the contact element 340 can be made of a soft material with low compressibility. An example can be a contact element 340 with high water content. Such a contact element 340 can lubricate the contact surface well and can adjust its shape locally to a small degree to accommodate the corneal surface upon docking, both factors reducing corneal wrinkling. At the same time, since the distal lens 330 and the affixation structure 350 do not allow for substantial radial or lateral deformations, such a contact element 340 still retains its overall shape and radii, thus providing a known and well-controlled optical path for the laser beam 112, minimizing its astigmatism and distortions.

In the embodiments above, the contact element 340 can be manufactured to be part of the contact portion 320 and thus part of the patient interface 300. In other embodiments, the contact element 340 can be provided as a separate element, for example hydrated in a pouch filled with an aqueous solution to prevent drying. Such contact elements 340 can be configured to be inserted into the contact portion 320 during a preparatory step of the ophthalmic surgery by a surgeon or other qualified personnel. In such embodiments, the contact portion 320 can be configured to accept the insertion of the contact element 340.

The contact portion 320 may accommodate the insertion of the contact element 340 by having an embodiment of the affixation structure 350 that can be an affixation groove, a support rim, an insertion structure, an interlocking structure, a slide-in structure, a pop-in structure, or a lock-in structure. In any of these embodiments, the affixation structure 350 can be configured to firmly affix the inserted contact element to the contact portion, and to prevent a more than 5% lateral expansion or bulging of the contact element upon the docking to the eye.

Further, in some embodiments, the contact portion 320 can include an embodiment of the rigid distal lens 330, having a distal surface with a distal radius of curvature within 5% of a proximal radius of curvature of a proximal surface of the contact element 340. In these embodiments, the distal lens 330 can form an extended contact with the contact element 340 upon its insertion, and can prevent a more than 5% radial deformation of the contact element upon the docking to the eye. As discussed above, the contact element 340 can be flexible but have low compressibility, an example of which can be materials with high water content.

Because of the outlined embedding geometry of the distal lens 330 and the affixation structure 350 and because of its low compressibility, the contact element 340 is largely prevented from bending, deforming, stretching, compressing and bulging once inserted into the contact portion 320, thus retaining its shape to a high degree when docked to the eye.

In these embodiments, while the contact element 340 can broadly match the structure and the radii of the central cornea and that of the sclera, small mismatches can remain as the precise values of these radii vary from patient to patient. Therefore, when docking the patient interface 300 to the eye, the central-cornea 21 and the contact element 340 may still need to deform to a small degree to accommodate these remaining small mismatches. As just outlined, in some embodiments, the distal lens 330, the affixation structure 350, and the central radius of curvature Rc can be selected such that they largely prevent the contact element 340 from deforming, stretching, and bending. Moreover, a material of the contact element 340 can be selected to make the compressibility of the contact element 340 low, thus preventing a compression of the contact element 340 as well. In such designs of the contact element 340, the central-cornea 21 may deform to a considerably larger degree than the contact element 340 upon docking. In numerical terms, a change of the radius of curvature of the central-cornea R(central-cornea) can be greater than a change of the central radius of curvature Rc of the contact element 340: ΔR(central-cornea) >ΔRc. In other embodiments, the central corneal deformations can be substantially larger than the deformations of the contact element 340 upon docking. The docking of these embodiments can be characterized by ΔR(central-cornea) >3ΔRc, ΔR(central-cornea)>5ΔRc and in some embodiments ΔR(central-cornea)>10ΔRc.

The choice of material of the contact element 340 can play a role in ensuring the above described attributes. In some embodiments, the contact element 340 can include a contact material that forms a lubricating film at the surface of the cornea. The lubrication can be made effective by a surface of the contact element 340 including a hydrophilic material. Hydrophilic materials not only lubricate efficiently, they can also reduce fogging of the contact element 340 which otherwise could present a problem during docking.

An embodiment of the contact material of the contact element 340 can be hydrogel. Typically, hydrogel can include a blend of fluorosilicone and hydrophilic monomers. Various embodiments of hydrogel can have widely varying water content, having different lubricating and optical properties and different compressibilities. By some classifications, a hydrogel is referred to as having low water content if its water content (by refractometer or by weight) is in the 10-50% range, in some cases in the 30-50% range, medium if the water content is in the 50-70% range, and high, if the water content is above 70%. The water content can be reached and maintained by hydrating the contact element 340 in an aqueous solution, an example of which can be saline.

Once hydrated, the contact element 340 can have a hydrated index of refraction in the range of 1.32-1.44, providing a close match with the index of refraction of the cornea, about 1.37.

The higher the water content, the more the contact element 340 is lubricating the contact surface with the central-cornea 21, further reducing the causes of wrinkling.

FIG. 3 also shows that the contact portion 320 can include a suction ring or suction skirt 322, to be coupled to a suction system through a suction port 324, to receive a suction from the suction system, and to apply the suction of the suction system to a contact space between the patient interface 300 and the eye 20 to dock the patient interface 300 to the eye firmly.

FIG. 3 also illustrates that in some embodiments of the patient interface 300, the attachment portion 310 and the contact portion 320 can be integrated portions of the patient interface 300. They can be firmly integrated during the manufacturing process, sometimes even formed from the same single plastic material.

Figure 4:
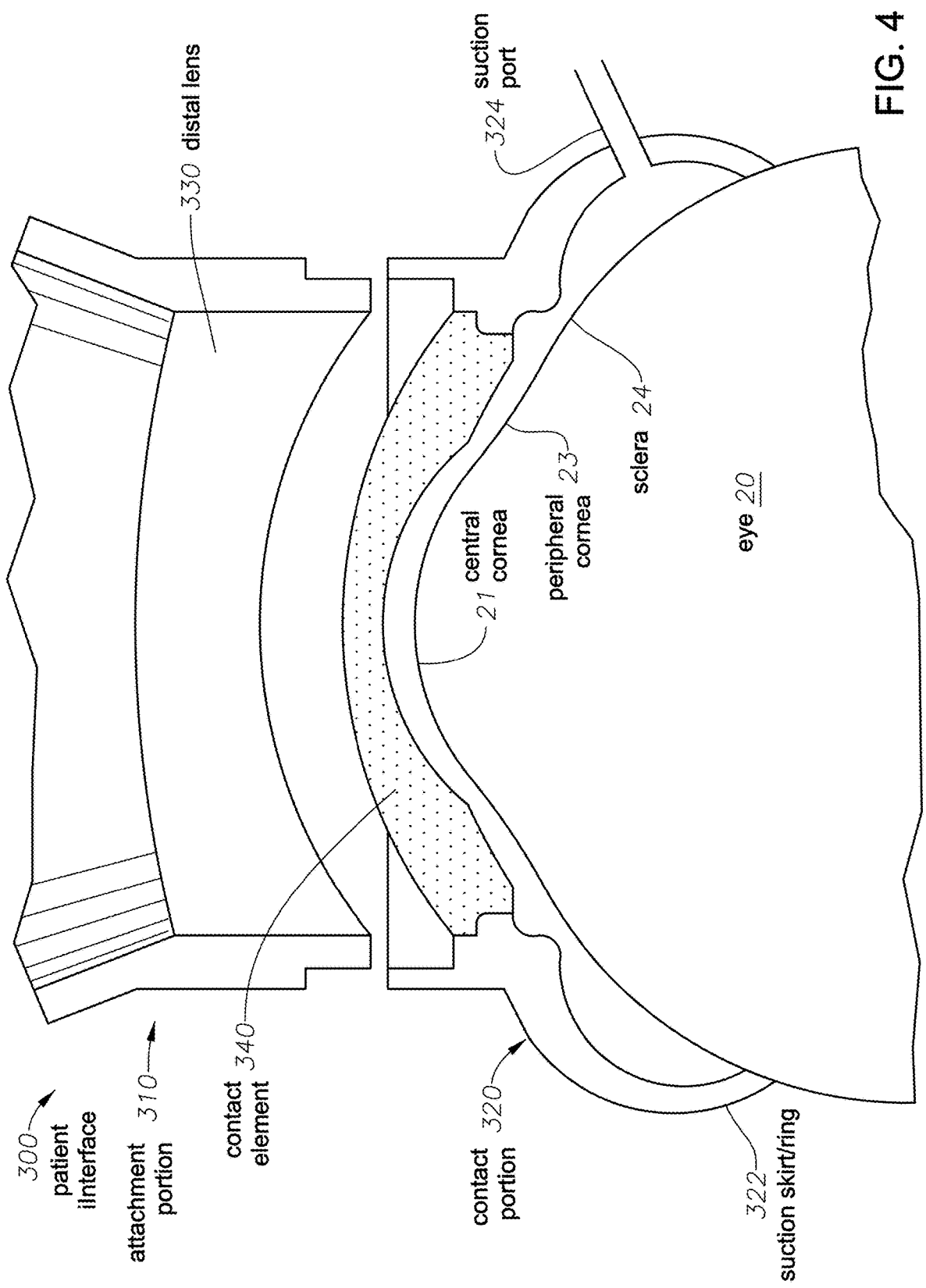
FIG. 4 illustrates a two-piece patient interface with a bi-radial contact element.

FIG. 4 illustrates that in some other embodiments, the attachment portion 310 can be separate from the contact portion 320. In such embodiments, the freely movable contact portion 320 can be first docked to the eye 20 with ease. Once the eye 20 is captured by the contact portion 320, the contact portion 320 can be used to manipulate and align the eye 20 with the attachment portion 310 that is harder to move since it is attached to the hard-to-adjust ophthalmic laser system 100. Once alignment is achieved, the contact portion 320 can be coupled to the attachment portion 310.

FIG. 5 illustrates a method 400 of docking a patient interface to an eye. Method 400 can include the following steps. Step 410 can include determining R(central-cornea), a radius of curvature of a central portion of a cornea, and R(peripheral-cornea-sclera), a radius of curvature characteristic of a peripheral portion of the cornea and a sclera of a procedure eye. For example, R(peripheral-cornea-sclera) can be a value between R(peripheral-cornea) and R(sclera) of the eye. Step 420 can include selecting a contact element with a central portion having a central radius of curvature Rc and a peripheral portion having a peripheral radius of curvature Rp that is greater than Rc. In relation to step 420, the contact element can be selected to have Rc less than R(central-cornea)+1.0 mm, and Rp less than R(peripheralcornea-sclera)+1.0 mm. Finally, step 440 can include docking the patient interface of an ophthalmic surgical laser system with the selected contact element to the eye. In some embodiments of selecting 420, the contact element can be selected to have Rc less than R(central-cornea)+0.75 mm, and Rp less than R(peripheral-cornea-sclera)+0.75 mm. In yet other embodiments of selecting 420, the contact element can be selected to have Rc less than R(central-cornea)+0.5 mm, and Rp less than R(peripheral-cornea-sclera)+0.5 mm.

In the steps of the method 400, the elements can be related to the analogous elements of the embodiments of FIGS. 1-4. In particular, the patient interface can be the patient interface 300, the procedure eye can be the eye 20, the contact element can be the contact element 340 and the ophthalmic surgical system can be the ophthalmic surgical system 100.

As described before, contact elements with the above characteristics can match the bi-radial structure of the frontal surface of the eye. With the radii Rc and Rp in the described ranges, they can provide a close match to both the central-cornea and the sclera. As also described earlier, the central and the peripheral portions can meet at an edge that can have a stretching or ironing effect on the cornea, further reducing the wrinkling. This stretching or ironing effect can be particularly effective if the selecting 420 includes selecting a contact element with a central radius of curvature Rc less than R(central-cornea).

The method 400 can further include inserting the selected contact element into the patient interface before docking, in embodiments where the contact element is provided separately from the patient interface. In some of these embodiments, a manufacturer can provide a patient interface and a set of contact elements for the operating surgeon. After the surgeon determines R(central-cornea) and R(peripheral-cornea-sclera), she or he can select the contact element whose central radius of curvature Rc and peripheral radius of curvature Rp are the most suitable in light of the determined radii R(central-cornea) and R(peripheral-cornea-sclera), and thus promise to best achieve the surgical goals.

In other embodiments, the contact element can be already installed or inserted into the patient interface during manufacture. In these embodiments, the selecting 420 can include selecting the patient interface from a set of patient interfaces that has the selected contact element.

In some embodiments of the method 400 the determining 410 can include generating a depth-image of an anterior portion of the eye and determining R(central-cornea) and R(peripheral-cornea-sclera) from the depth-image. The depth-image can be generated by an Optical Coherence Tomography (OCT) system, a Scheimpflug system, or a slit lamp.

While this document contains many specifics, these should not be construed as limitations on the scope of the invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination. Also, variations and enhancements of the described implementations, and other implementations can be made based on what is described.

What is claimed is:

1. A contact element of a patient interface for an ophthalmic system, the contact element comprising a distal surface and a proximate surface opposite the distal surface, the distal surface configured to interface with an eye of a patient, the contact element further comprising:

a transparent central portion with a central radius of curvature on the distal surface;

a transparent peripheral portion with a peripheral radius of curvature on the distal surface, the central radius of curvature on the distal surface smaller than the peripheral radius of curvature on the distal surface; and an edge structure where the transparent central portion and the transparent peripheral portion meet;

wherein the proximate surface of the contact element includes a proximate surface radius of curvature that is larger than that of the transparent central portion.

2. The contact element of claim 1, wherein the contact element is most narrow at an apex of the transparent central portion.

3. The contact element of claim 1, wherein the contact element is made of a hydrogel.

4. The contact element of claim 3, wherein the edge structure is a region of the contact element and the hydrogel spans at least across the transparent peripheral portion, the edge structure, and the transparent central portion.

5. The contact element of claim 3, wherein the hydrogel includes a blend of fluorosilicone and hydrophilic monomers.

6. The contact element of claim 3, wherein the hydrogel includes between 50-70% water content.

7. The contact element of claim 3, wherein the hydrogel includes above 70% water content.

8. The contact element of claim 1, further comprising a stepped-feature at a peripheral edge of the contact element.

9. The contact element of claim 8, wherein the stepped-feature is shaped to interface with a suction ring.

10. A surgical system comprising:

a patient interface configured to be coupled to a surgical laser system, the patient interface comprising:

an attachment portion for interfacing with the surgical laser system; and a contact portion configured to interface with an eye of a patient, the contact portion including a contact element that comprises:

a transparent central portion with a central radius of curvature on an eye-facing surface;

a transparent peripheral portion with a peripheral radius of curvature on the eye-facing surface, the central radius of curvature on the eye-facing surface smaller than the peripheral radius of curvature on the eye-facing surface; and an edge structure where the transparent central portion and the transparent peripheral portion meet;

wherein an attachment-portion-facing surface includes an attachment-portion-facing radius of curvature that is larger than that of the transparent central portion;

wherein the attachment-portion-facing surface of the contact element is opposite the eye-facing surface.

11. The surgical system of claim 10, further comprising the surgical laser system, the surgical laser system including a laser beam-generating device and one or more optical elements to guide the laser beam to the patient interface.

12. The surgical system of claim 10, further comprising a depth-imaging system configured to provide depth information of the eye.

13. The surgical system of claim 12, the depth-imaging system comprising at least one of an optical coherence tomography (OCT) imaging system, a Scheimpflug imaging system, or a slit-lamp system.

14. The surgical system of claim 10, further comprising a video-imaging system configured to display a front video image of the eye.

15. The surgical system of claim 10, further comprising a fixation light source positioned to project a fixation light beam through the patient interface.

\* \* \* \* \*